United States Patent [19]

Camacho

[11] 4,300,884
[45] Nov. 17, 1981

[54] CASTING COLLAR FOR DENTAL IMPRESSION TRAY

[76] Inventor: Hector Camacho, 9972 66th Rd., Apt. 5-B, Forest Hills, N.Y. 11374

[21] Appl. No.: 125,326

[22] Filed: Feb. 28, 1980

[51] Int. Cl.³ ............................................. A61C 19/00
[52] U.S. Cl. ........................................ 433/74; 433/37
[58] Field of Search ................... 433/74, 53, 37, 34

[56] References Cited

U.S. PATENT DOCUMENTS

| | | | |
|---|---|---|---|
| 2,851,728 | 9/1958 | Spalten et al. | 433/74 |
| 3,436,829 | 4/1969 | Jermyn | 433/74 |
| 3,461,562 | 8/1969 | Cooper | 433/53 |
| 3,931,677 | 1/1976 | Tinder | 433/74 |
| 4,017,972 | 4/1977 | Glenn | 433/74 |
| 4,243,389 | 1/1981 | Eisner | 433/74 |

Primary Examiner—Gene Mancene
Assistant Examiner—John J. Wilson
Attorney, Agent, or Firm—Richard L. Miller

[57] ABSTRACT

A method and apparatus for facilitating the formation of dental castings utilizing a dental impression tray. A collar assembly is provided which is substantially oval and forms an upstanding peripheral enclosure around the dental impression tray. A rod transversely spans across the oval member and is retained in notches at the upper edge of the oval member. The rods pass through spherical coupling members from which depend dowel pins which can enter into the negative impression and are used for retaining the teeth which are subsequently formed by a casting process.

13 Claims, 15 Drawing Figures

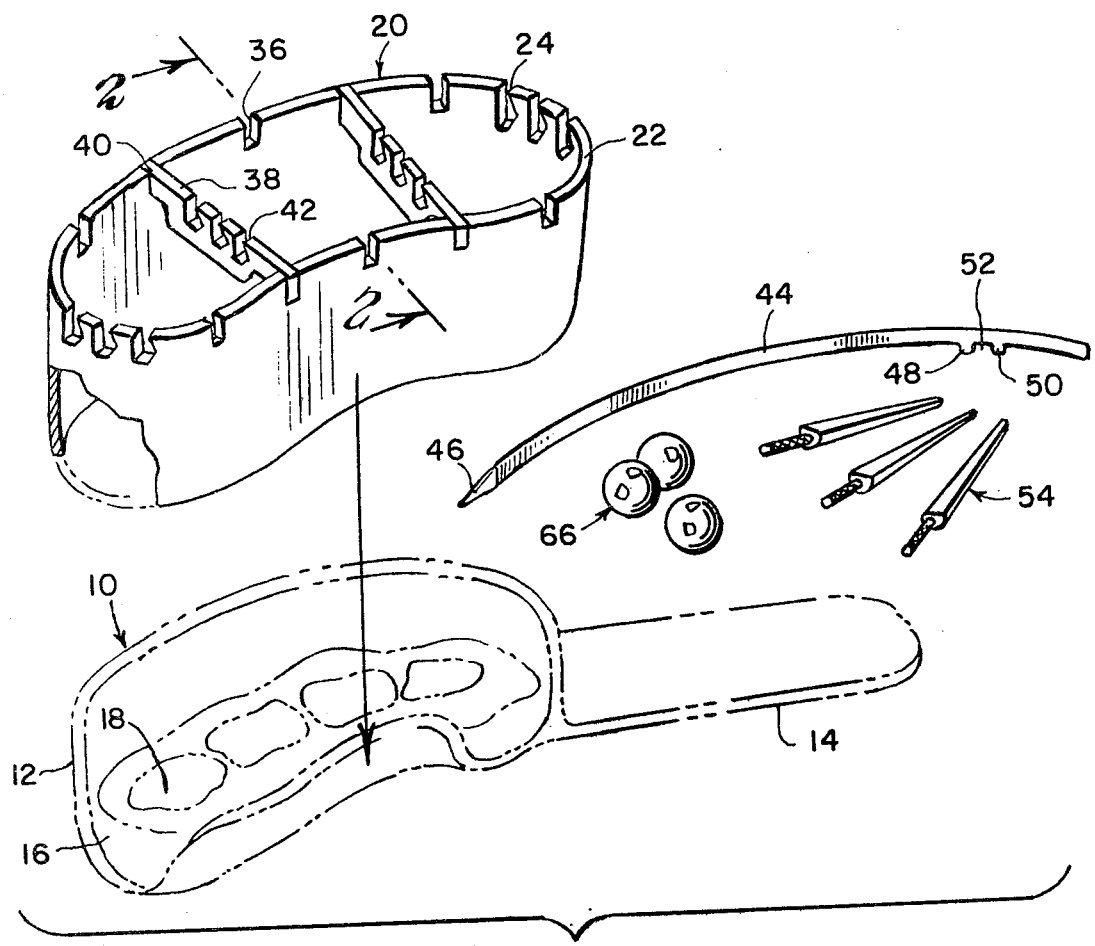
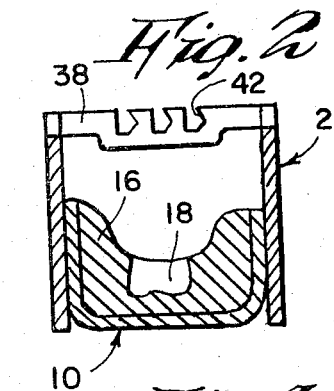
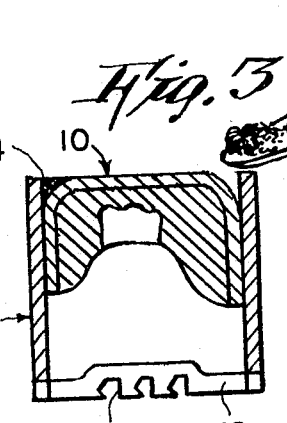
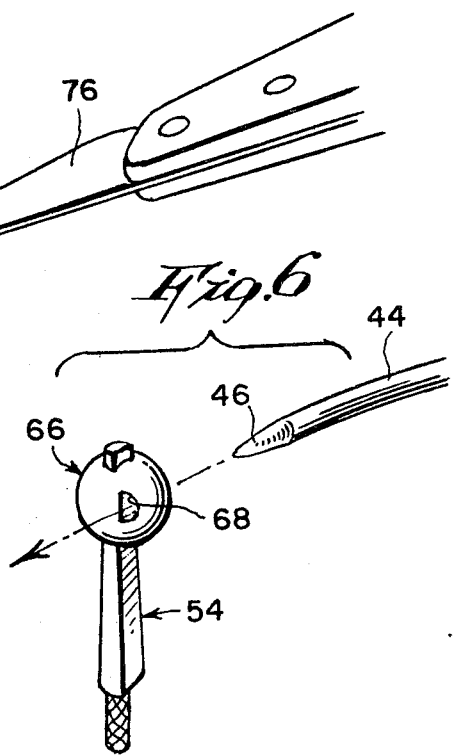
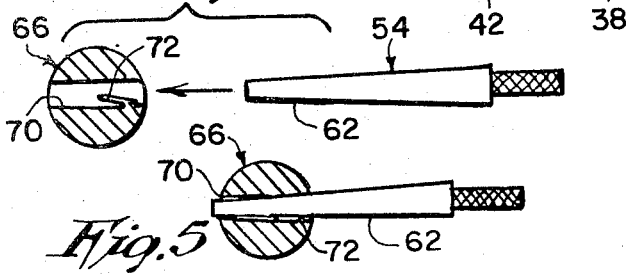

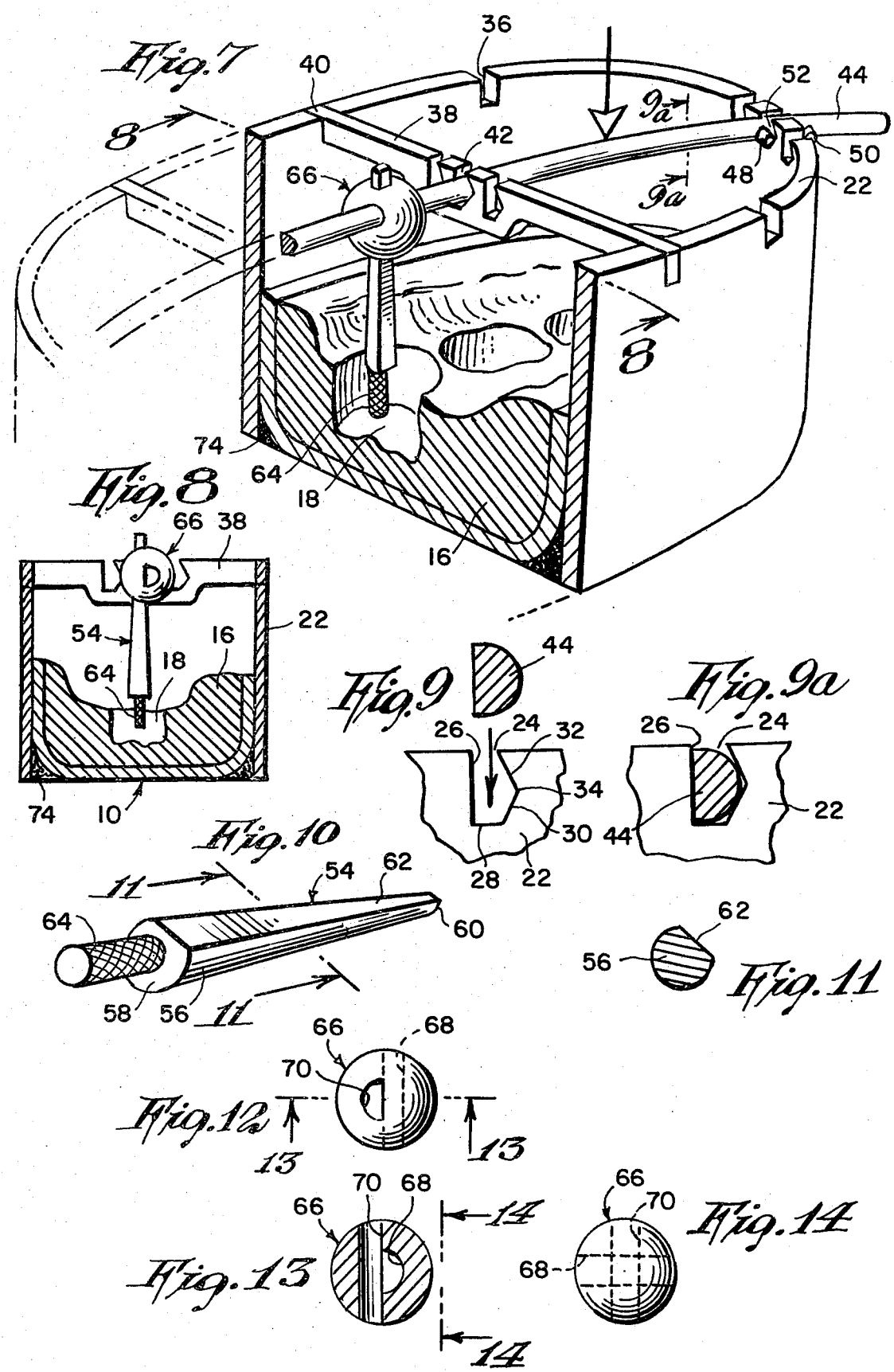

CASTING COLLAR FOR DENTAL IMPRESSION TRAY

BACKGROUND OF THE INVENTION

This invention relates to dental equipment, and more particularly to a reusable collar for a dental impression tray.

The use of dental castings for making teeth is well known in the art. Dentists and dental laboratories have numerous devices to utilize in the making of single teeth or bridges for replacement and reconstruction of damaged portions of the patient's mouth. The usual procedure involved requires the formation of a dental impression, or a negative, directly from the patient's mouth and using that negative to make a positive casting of the desired teeth or bridge.

Dental impression trays are generally utilized for this purpose. The trays are designed to fit sections of the mouth and accordingly numerous trays are available for different sections of the mouth. A casting material is placed in the tray and the patient bites down into the casting material to make the impression. The impression tray is then removed and strick wax is rolled out from sheets and placed about the dental impression tray to build up a protective wall about the tray to retain the material poured in to make the positive impression. Numerous types of holding devices are also inserted through the walls of the strick wax to hold the dowel pins which extend downwardly into the cavity in the negative impression and which will provide the support posts for the teeth. Such items as bobby pins are frequently utilized for holding the dowel pins.

Although this procedure has been widely accepted and utilized throughout the dental profession, much of it is quite primative, cumbersome and awkward. For example, the use of the red strick wax is exceedingly bothersome and time consuming. The wax must be cut from the sheets, fitted about the tray and molded to shape the particular dental tray. This is a most awkward part of the process.

Additionally, there is no secure method of holding the dowel pins in proper position. The use of bobby pins, or other such implements which are regularly used, is a most imprecise positioning technique and often prevents the proper positioning of the dowel pins in the cavity of the (preparation) negative impression. This is especially a problem where a large bridge section must be formed and more than one pin must be utilized for the section. When trying to pull up on the dies pins to remove the (bridge wax up) positively formed piece, the bridge section may be damaged or may even crack if the pins are not both positioned properly in the same section.

Although the use of the strick wax, the bobby pins, and other such primative devices present difficulties in use, nevertheless, they still continue to be used by the dental profession as well as by dental laboratories, mainly for lack of any improved and more precise devices for facilitating the formation of dental castings.

BACKGROUND OF THE INVENTION

It is accordingly an object of the present invention to provide improved methods and apparatus for forming dental castings which avoid the aforementioned problems of prior art devices.

Yet another object of the present invention is to provide a reusable collar for a dental impression tray which will facilitate the formation of dental castings.

Still another object of the present invention is to provide a preformed collar for a dental impression tray which includes support and positioning means for properly placing the dowel pins into cavities within the negative impression (preparation) held by the impression tray.

Still a further object of the present invention is to provide a collar for enclosing the periphery of a dental impression tray which supports rods extending across its top from which depend dowel pins which can be used to hold the positively formed teeth.

Another object of the present invention is to provide a collar, rod, and spherical coupling device for use in the formation of dental castings.

Yet another object of the present invention is to provide a unique method of forming a dental casting which is easier to implement, less time consuming, and more accurate than prior art methods.

Briefly, in accordance with the present invention, there is provided a collar for a dental impression tray which includes a preformed substantially oval member having a continuous thin outer wall. The oval member forms an upstanding peripheral enclosure surrounding a dental impression tray. The oval member has an open top and bottom. A plurality of notches are formed about the upper edge of the wall at its opposing ends for supporting depending dowel pins which are positioned to engage the teeth which are being cast in the tray.

At least one rod spans across the longer dimension of the oval member and is securely retained within the opposite pairs of notches. A spherical coupling member is utilized for interconnecting the rod with the depending dowel pins.

The invention further comprises a method forming the dental castings, comprising the steps of positioning a preformed oval collar about a dental tray having therein the dental impression. The oval collar is sealed to the dental tray at its bottom. Dowel pins are then depended from an elongated rod which extends across the top of the oval collar. The casting material can then be poured into the impression tray and the rest of the procedure for forming the teeth or dental bridge is carried out as in the prior art.

The particular collar can be made of plastic material whereby it is reusable. By preshaping the plastic collar to conform to the particular trays utilized, a proper fit between the collar and the tray will be attained. Each time a tray is selected its appropriate collar is utilized with the tray.

The aforementioned objects, features and advantages of the invention will, in part, be pointed out with particularity, and will, in part, become obvious from the following more detailed description of the invention, taken in conjunction with the accompanying drawings which form an integral part thereof.

BRIEF DESCRIPTION OF THE DRAWINGS

In the drawings:

FIG. 1 is an exploded perspective view of the components of the invention prior to their assembly with a dental impression tray;

FIG. 2 is a cross sectional side elevational view taken along line 2—2 of FIG. 1, and showing the collar being fitted around the tray;

FIG. 3 is a view similar to that shown in FIG. 2 however it is inverted and shows the sealing of the collar to the tray;

FIG. 4 is an exploded view of the dowel pin positioned for assembly within the spherical coupling member;

FIG. 5 shows the parts of FIG. 4 in the assembled condition;

FIG. 6 is an exploded view showing the assembly of FIG. 5 positioned for insertion of the rod therein;

FIG. 7 is a perspective cross sectional view of the final assembly;

FIG. 8 is a cross section elevational view taken along line 8—8 of FIG. 7;

FIG. 9 is a detailed view showing the insertion of the rod into the notches;

FIG. 9A shows the assembled rod in the notch and is taken along line 9—9 of FIG. 7;

FIG. 10 is an enlarged perspective view of the dowel pin;

FIG. 11 is a cross sectional view of the dowel pin taken along line 11—11 of FIG. 10;

FIGS. 12, 13 and 14 are three views taken along three directions of the spherical coupling member, with FIG. 13 being in cross section.

In the various figures of the drawing, like reference characters designate like parts.

DESCRIPTION OF THE PREFERRED EMBODIMENTS

Referring now to the drawings, and more specifically to FIGS. 1 and 7, the usual procedure in forming dental castings is to utilize a dental impression tray, shown generally at 10. The tray has a generally U-shaped wall 12 and is generally curved so as to fit a portion of the mouth. A laterally extending handle 14 is provided so that the dentist or technician can hold the tray while it is placed in the patient's mouth. Some type of casting material 16 is generally placed into the tray and the tray is then inserted into the patient's mouth. The patient bites down to form the cavities or impressions 18. The tray is then removed after the material has hardened so as to form a negative impression of the tooth section.

The dental tray is then usually taken and subsequently utilized as a mold for making a positive impression of the teeth to be replaced or the bridge section. In order to make the positive impression, it is necessary to pour casting material such as epoxy or stone, etc., into the mold. However, the dental tray has walls that are not high enough to accommodate the casting material which must be poured into the tray. Therefore, the walls on the side of the impression tray are usually built up with a type of strick wax material. The strick wax material is usually red and comes in flat sheets with paper inbetween. A section is cut off and it is wrapped around the impression tray and then must be held together by means of some type of sealing wax such as sticky wax. The strick wax must be cut and shaped to suitably fit the particular impression tray. This is usually a difficult procedure.

In the present invention, there is provided a preformed collar shown generally at 20. The collar is typically formed of plastic material and is substantially oval in shape, however the particular shape is bent so as to suitable fit the particular tray. Since there are approximately 12 impression trays that are used for the entire mouth, there would be a similar number of collars, each adapted to fit a particular dental tray. However, since they are made out of plastic or other similar material, they can be easily cleaned and reused. Therefore, a set will be provided with each tray having its corresponding collar and each time the tray is used its associated collar will be utilized with it.

The collar 20 is formed of thin walled material 22 having an open top and bottom. Notches 24 are formed downwardly from the upper edge of the end portions of the wall. As can best be seen in FIG. 9, the notches 24 are substantially shaped in D-fashion. Each notch includes a vertical side wall 26, a horizontal bottom wall 28, and an arrow shaped opposing side wall having the angular portions 30 and 32 meeting at the vertex 34.

The notches formed at the opposing ends are substantially colinear with each other. Along the side walls, there are formed U-shaped grooves 36. The grooves on opposing side walls are colinearly positioned. Located within selected opposing pairs of the grooves is a support rib 38 which includes ends 40 which can tightly fit within the grooves and be held therein. The supporting ribs 38 also include D-shaped notches 42 which are again colinear with opposing pairs of notches at the opposite end walls.

There is additionally provided a rod 44 having a D-shaped cross section as can best be seen in FIG. 9. The rod has its front end tapered so as to form a spear-like front edge 46. At its rear end, the rod has two downwardly facing projections 48, 50 so as to form an indentation therein 52.

There are also provided dowel pins 54. The dowel pin can best be seen in FIG. 10 as comprising an elongated member 56 which is tapered from a wide end 58 to a narrow end 60. One side face is flattened 62. Extending from the wide end face 58 is a cylindrical stem 64 having a knurled outer surface.

There are also provide spherical coupling members shown generally at 66. These can be seen in more detail in FIGS. 12–14 as well as FIGS. 4–6. The spherical members have two non-intersecting orthogonal channels. Both channels are substantially D-shaped in cross section. A first horizontal channel 68 is D-shaped and is available for receiving therethrough the D-shaped rod 44, as shown in FIG. 6. A second, vertical D-shaped channel 70 is available for receipt therethrough of the tapered end of the dowel pins 54 as shown in FIGS. 4 and 5. In order to insure that the dowel pins remain in place, an inwardly extending tab or finger 72 extends inwardly into the channel 70 to lock against the flat end 62 of the dowel pin 54.

In utilizing the aforedescribed devices, after the dental impression tray is removed from the patient's mouth and the contents therein are permitted to harden, in the usual prior art manner, the collar 20 is placed about the dental tray 10, as shown in FIG. 2. The dental tray is then inverted and the bottom edge of the collar is sealed to the bottom of the dental tray by means of sticky wax 74. The wax can be applied by means of a tool such as a spatula 76. Such sealing at the bottom is well known in the art and has been used even in connection with the strick wax. However, in the prior art, since the strick wax had to be shaped, a great amount of such sealing wax was required and it was awkward to apply it. In the present situation, since the collar is preshaped to fit the particular impression tray, it is a rather easy matter to seal the bottom of the collar to the bottom of the impression tray.

The rod assembly can then be put together. If the dowel pins have not been already inserted into the spherical coupling members 66, then the dowel pins are inserted with the tapered ends extending into the channel containing the inwardly extending tab, as shown in FIG. 4. The dowel pins are pushed as far as they can go so that they will be held securely in the spherical coupling members, as shown in FIG. 5. As many dowel pins as are needed can be prefixed in their respective coupling members.

After the dowel pins have been assembled to their coupling members, the rod, with the spear end forward, is threaded through the other channel 68. The spherical members 66 can slide along the rod so as to vertically position them in the desired locations. The rod is then snapped into place across the top of the collar by selecting suitable notches. It will be noted that since the rod is D-shaped, and the corresponding notches are also substantially D-shaped, the rod will snap into place in the notch and will be securely held and prevented from rotation.

At the same time, the rod is laterally positioned so that the downwardly depending projections 48, 50 span on either side of the collar wall 22 so that the wall is held within the formed depression 52 as shown in FIG. 7. This will prevent lateral sliding of the rod across the collar.

If additional support is needed for the rod, the support ribs 38 can be placed in position before the rod is assembled. These will be placed in appropriate grooves 36 and span transversely across the oval shaped member. When inserted, the rod would also be snapped in the notches 42 contained in these support ribs.

Once assembled, the dowel pins will be downwardly depending at the desired location directly within the particular cavities 18 of the preparation which are needed for the formation of the teeth. The knurled ends 64 of the dowel pins will extend the proper distance into the cavity of the preparation so that they will support the teeth which are subsequently formed. Should the dowel pins not be exactly positioned as desired, they can be slightly slid along the rod 44 so that they will be accurately positioned. At the same time, the rod itself can be shifted by moving it into different pairs of notches so as to properly position it.

By making the rod out of flexible plastic material, it can be bent into any desired shape so as to suitably position the dowel pins as needed. At the same time, the spherical coupling means can also be made out of plastic material so that it can also be cleaned and reused each time as can be the collar and rod. The dowel pins, as in the prior art, can be made of a metal material.

Once assembled, as shown in FIGS. 7 and 8, the suitable type of casting material such as epoxy, can be poured into the mold and the positive impression will be formed. Typically, the use of epoxy to form the teeth and a subsequent stone material to retain the teeth will be utilized.

There has been disclosed heretofore the best embodiments of the invention presently contemplated. However, it is to be understood that various changes and modifications may be made thereto without departing from the spirit of the invention.

I claim:

1. A collar assembly for a dental impression tray, comprising:
   a preformed substantially oval member having a continuous, thin, outer wall which forms an upstanding peripheral enclosure surrounding a dental impression tray, and having an open top and bottom;
   a plurality of notches formed about the upper edge of the wall and opposing ends thereof for supporting depending dowel pins positioned to engage teeth being cast in the tray;
   removable coupling means for securely retaining the dowel pins in place while permitting longitudinal, lateral and axial positioning of the dowel pins comprising
   at least one rod spanning across the longer dimension of the oval member and retained within opposing ones of said notches, and at least one dowel depending therefrom.

2. A collar assembly as in claim 1, and further comprising substantially spherical coupling members having non-intersecting orthogonal channels formed therethrough, said rod passing through one of said channels and said dowel pin retained within the other of said channels.

3. A collar assembly as in claim 1, and further comprising support ribs transversely spanning across the top of the shorter dimension of said oval member, and including a plurality of notches formed at the top edge thereof which are colinearly positioned with respect to the notches at opposing ends of said oval member, said rods passing through said notches in said support ribs.

4. A collar assembly as in claim 3, wherein said outer wall further comprises grooves formed about the upper edge thereof at opposing lateral sides for positioning and supporting said support ribs.

5. A collar assembly as in claim 1, wherein said rods are D-shaped in cross section, and said notches are matingly shaped to permit a snap fit of the rods in the notches and to prevent rotation of the rods therein.

6. A collar assembly as in claim 2, wherein said rods and the channel receiving said rods are both D-shaped in cross section.

7. A collar assembly as in claim 2, and further comprising a tab inwardly projecting into the channel receiving said dowel pin for grasping the dowel pin and preventing its removal from the channel.

8. A collar assembly as in claim 2, wherein said dowel pins are tapered toward one end thereof, have one elongated side thereof flattened, and includes a knurled stem colinearly extending from the wider end thereof, said tapered end being inserted within its corresponding channel in said coupling member.

9. A collar assembly as in claim 2, wherein said rod further comprises spaced apart ribs at one end thereof for straddling said wall of said oval member to thereby restain said rod from lateral movement, and a spear shaped end at the opposite end thereof for facilitating passing the rod through the channels in the coupling members.

10. A collar assembly as in claim 1, wherein said oval member is formed of reusable plastic material and is sized to fit a specified impression tray.

11. A method of forming dental castings, comprising the steps of:
   positioning a preformed oval collar about a dental tray having therein a dental impression;
   sealing the bottom of the oval collar to the dental tray;
   depending dowel pins from an elongated rod;
   spanning the elongated rod across the top of the oval collar; and
   adjusting the depending dowel pins in a lateral, longitudinal and axial direction while they are retained depended from the rod;

said step of depending further comprising inserting a dowel pin in a channel of a spherical coupling member, and passing the rod through an orthoginally non-intersecting channel in the spherical coupling member.

12. A method of forming dental castings, comprising the step of:
- positioning a preformed oval collar about a dental tray having therein a dental impression;
- sealing the bottom of the oval collar to the dental tray;
- depending dowel pins from an elongated rod;
- spanning the elongated rod across the top of the oval collar; and
- adjusting the depending dowel pins in a lateral, longitudinal and axial direction while they are retained depended from the rod;

said step of spanning further comprising the step of inserting the rod into receiving notches at opposite ends of the oval member.

13. A method of forming dental castings, comprising the steps of:
- positioning a preformed oval collar about a dental tray having therein a dental impression;
- sealing the bottom of the oval collar to the dental tray;
- depending dowel pins from an elongated rod;
- spanning the elongated rod across the top of the oval collar;
- adjusting the depending dowel pins in a lateral, longitudinal and axial direction while they are retained depended from the rod; and
- positioning support ribs transversely across the top of the oval member for providing additional support for the rods.

* * * * *